United States Patent
Ketkar et al.

(10) Patent No.: US 6,606,899 B1
(45) Date of Patent: Aug. 19, 2003

(54) TOTAL IMPURITY MONITOR FOR GASES

(75) Inventors: Suhas Narayan Ketkar, Allentown, PA (US); Seksan Dheandhanoo, Quakertown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 15 days.

(21) Appl. No.: 09/611,842

(22) Filed: Jul. 7, 2000

(51) Int. Cl.$^7$ .................. G01N 19/10; G01N 27/64; G01T 1/18; H01J 47/02
(52) U.S. Cl. .................. 73/31.02; 73/81.03; 250/384; 250/387; 324/469
(58) Field of Search .................. 73/31.01, 31.02, 73/31.03, 23.2; 250/384, 387, 432 R; 324/469

(56) References Cited

U.S. PATENT DOCUMENTS

| | | | |
|---|---|---|---|
| 2,387,550 A | * 10/1945 | Winkler | 73/23.2 |
| 3,566,107 A | * 2/1971 | Taylor | 73/31.01 |
| 3,601,609 A | 8/1971 | Yauger, Jr. | 250/44 |
| 3,617,734 A | * 11/1971 | Chaudet et al. | 73/31.01 |
| 3,638,397 A | * 2/1972 | Charlton | 95/56 |
| 3,699,333 A | 10/1972 | Cohen et al. | 250/41.9 TF |
| 3,835,328 A | * 9/1974 | Harris et al. | 250/308 |
| 4,007,624 A | * 2/1977 | Chantry et al. | 73/23.2 |
| 4,075,550 A | * 2/1978 | Castleman et al. | 324/469 |
| 4,137,453 A | * 1/1979 | Siegel | 250/382 |
| 4,238,678 A | 12/1980 | Castleman et al. | 250/381 |
| 4,261,698 A | 4/1981 | Carr et al. | 23/232 E |
| 4,336,454 A | * 6/1982 | Bryant et al. | 250/381 |
| 4,390,784 A | 6/1983 | Browning et al. | 250/287 |
| 4,450,409 A | * 5/1984 | Castleman et al. | 250/384 |
| 4,777,363 A | 10/1988 | Eiceman et al. | 250/286 |
| 4,864,141 A | * 9/1989 | Lewiner | 250/381 |
| 4,879,472 A | * 11/1989 | Wise et al. | 250/379 |
| 5,047,723 A | * 9/1991 | Puumalainen | 324/464 |
| 5,114,677 A | * 5/1992 | Steele et al. | 324/469 |
| 5,153,520 A | * 10/1992 | Dumbeck | 324/469 |
| 5,200,614 A | 4/1993 | Jenkins | 250/286 |
| 5,281,915 A | * 1/1994 | Takahama et al. | 324/469 |
| 5,543,331 A | * 8/1996 | Puumalainen | 73/31.03 |

FOREIGN PATENT DOCUMENTS

| | | | |
|---|---|---|---|
| EP | 0198154 | 11/1994 | G01N/27/62 |
| EP | 0528426 | 1/1998 | G01N/27/64 |
| FR | 2583878 | * 12/1986 | 73/23.2 |
| GB | 1509189 | * 5/1978 | |
| GB | 2255671 | 11/1992 | H01J/49/26 |

OTHER PUBLICATIONS

Skoog, D. A. Principles of Instrumental Analysis, 1984, Saunders College Publishing, Third Edition, pp. 523–565.*
Lovelock, J. E. "Ionization Methods for the Analysis of Gases and Vapors", Analytical Chemistry, Feb. 1961, vol. 33, No. 2, pp. 162–178.*
"Nanotrace II", http://www.delta-f.com/ProductSheets/PNT2Page2.htm, Aug. 2001, pp. 1–2.*

* cited by examiner

Primary Examiner—Edward Lefkowitz
Assistant Examiner—Michael Cygan
(74) Attorney, Agent, or Firm—Geoffrey L. Chase

(57) ABSTRACT

A device for measuring a total concentration of impurities in a sample gas is provided which includes a housing having an inlet to allow the sample gas to enter the housing, an emitter to generate ions from the sample gas, a field gradient to accelerate the ions toward a collector, the collector adapted to measure total ions, and an outlet to allow the sample gas to exit the housing, whereby a change in total ions received by the collector indicates a change in the total concentration of impurities in the sample gas.

19 Claims, 1 Drawing Sheet

TOTAL IMPURITY MONITOR FOR GASES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to impurity monitors for gases, and, in particular, to a device for monitoring the total impurities in ultra high purity gases.

Ultra high purity gas is needed by, for example, the semiconductor fabrication industry where, according to current industry specifications, impurities typically may be required that are less than one part per billion. As the industry matures, these levels are expected to go even lower. At the present time, the practice in the industry is to certify compliance with these specifications at the time of commissioning of the gas delivery system that delivers these ultra high purity gases. Thereafter, real time upset monitors are used to detect large changes in the concentration of impurities. The main reason for not monitoring continuously, in real time compliance with the industry specifications, is the prohibitive cost of sophisticated analytical instruments needed for this purpose.

The objective of the present invention is to provide an inexpensive device that can monitor changes in the total impurity content in ultrahigh purity gases being supplied to, for example, the semiconductor industry.

At the present time, atmospheric pressure ionization mass spectrometry (APIMS) is the only practical analytical technique capable of achieving detection limits significantly below impurity levels of less than one part per billion. Attempts have been made to simplify this instrument so as to reduce its cost. For example, attempts have been made to devise a sample switching manifold so that one can use a single APIMS instrument and sample multiple sample points and/or gas streams. Efforts are also being made to improve the sensitivity of other analytical instruments so that they can be used for monitoring compliance with the above noted industry specifications where it is desired to have impurities at levels less than one part per billion.

One instrument is commercially available that can meet the one part per billion specification for trace oxygen in gases. This is the NanotraceJ $O_2$ analyzer made by Delta F Corporation of Massachusetts. However, this device is sensitive to only oxygen gas, whereas an APIMS is sensitive to other impurities as well.

Unexamined Japanese Patent Kokai 9-6 1402 directed to a device for measuring concentration of impurities in gases describes the use of a discharging chamber to measure concentration of impurities in gases. A corona discharge is established between a needle and an electrode. A high voltage constant current source is used for the discharge so that the discharge current is maintained at a constant level. The sample gas flows through this discharge. The sample gas is supplied via a component separating means such as a chromatograph or a membrane. As the impurity concentration of the sample gas changes, the voltage needed to maintain a fixed current changes. The change in voltage is a measure of the impurity concentration.

Although the Unexamined Japanese Patent does not explicitly mention the use of this device to monitor the changes in the total impurity concentration of the sample gas, if one were to sample the gas without any component separating means, this device can be used to monitor changes in total impurity concentration.

A major problem with using a corona discharge device is that, over time, the tip of the discharge needle erodes, thereby changing the needle to electrode distance. This change in distance will cause a change in voltage needed to establish a constant current. Thus, the output of this device will slowly change over time without any changes in the impurity concentration in the sample gas.

Certain ion mobility spectrometers have a somewhat similar structure to that of the present invention. See, for example, U.S. Pat. No. 4,238,678, which includes a housing, an ionizing source such as $Ni^{63}$, a shutter grid and a collector. However, in this type of spectrometer, the shutter is periodically opened and an ion cloud is allowed to enter the drift region of the spectrometer analyzer cell. The ion cloud moves in the drift region under the influence of an electric field. The ions are separated into different groupings, depending upon their mobilities. As each separated ion grouping arrives at the collector plate at the end of the drift region, an electrical pulse is detected by a detection circuit. A multichannel analyzer is typically used to average spectra from multiple openings of the electric shutter to produce an ion mobility spectrum. The present invention does not use a shutter that is periodically opened and closed.

It is principally desired to provide a novel device for measuring the total concentration of impurities in a sample gas.

It is further desired to provide a novel device for measuring the total concentration of impurities in a sample gas that can detect very low levels of impurities in the sample gas.

It is still further desired to provide a novel device for measuring the total concentration of impurities in a sample gas that can detect levels of impurities of less than one part per billion in the sample gas.

It is also desired to provide a novel device for measuring the total concentration of impurities in a sample gas continuously and in real time.

It is also desired to provide a novel device for measuring the total concentration of impurities in a sample gas continuously and relatively inexpensively.

It is further desired to provide a novel device for measuring the total concentration of impurities in a sample gas that yields a consistent response through the lifetime of the device.

It is further desired to provide a novel device for measuring the total concentration of impurities in a sample gas that does not require a high voltage power supply to generate electrons.

It is further desired to provide a novel device for measuring the total concentration of impurities in a sample gas that is simple and inexpensive.

BRIEF SUMMARY OF THE INVENTION

The present invention is directed to a device for measuring a total concentration of impurities in a sample gas which includes a housing having an inlet to allow the sample gas to enter the housing, an emitter to generate ions from the sample gas, and a field gradient to accelerate the ions toward a collector. The collector measures total ions, and an outlet on the housing allows the sample gas to exit the device. A change in total ions measured indicates a change in a total concentration of impurities in the sample gas. Preferably, the emitter is a radioactive foil of $Ni^{63}$ that emits approximately 67 keV electrons and has a strength of 1 milli Curie. Additionally, it is preferable that the collector is connected to an amplifier which is used to detect current striking the collector. It is also desirable that a ground base preamplifier is connected between the collector and the amplifier such that the voltage at the collector is at zero volts. Optionally, at least one grid electrode is located in the housing between the emitter and the collector to facilitate ions in moving from the $Ni^{63}$ β emitter to the collector. Alternatively, the inside of the housing includes a resistive coating to facilitate ions in moving from the emitter to the collector. The housing is preferably fabricated from metal, such as electro polished stainless steel that can be heated to at least 200 degrees Celsius.

DETAILED DESCRIPTION OF THE INVENTION

Figure 1:
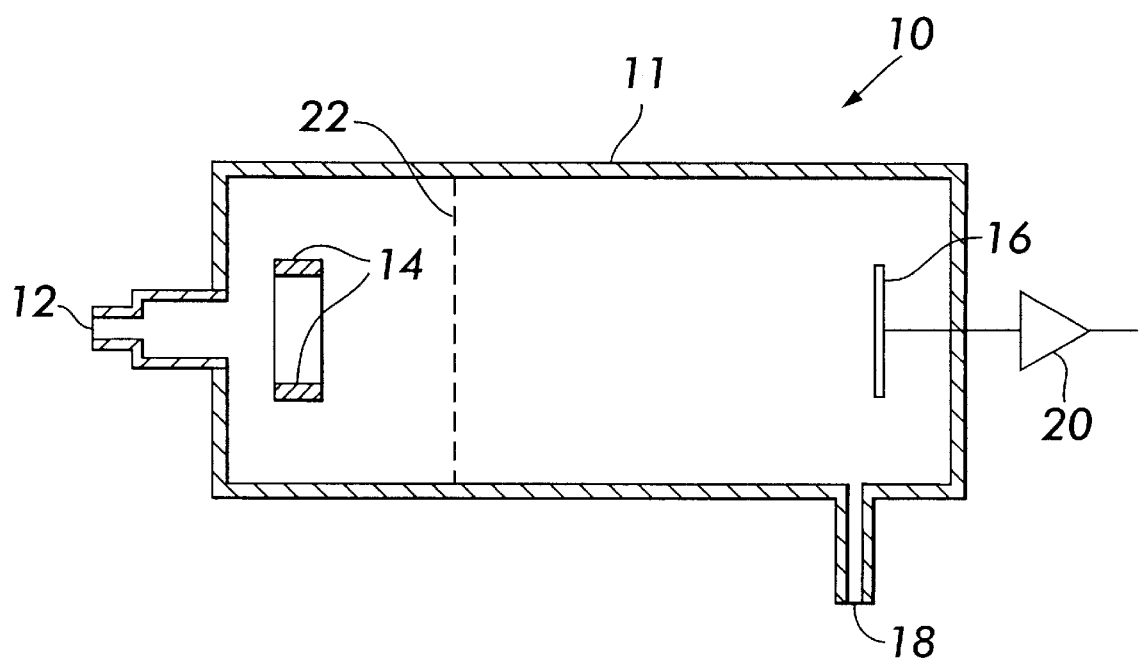
FIG. 1 is a schematic of a total impurity monitor for gases in accordance with one preferred embodiment of the present invention.

Referring now to FIG. 1, there is shown a total impurity monitor for gases 10 in accordance with one preferred embodiment of the present invention. The total impurity monitor for gases 10 is a device for measuring the total concentration of impurities in a sample gas, and has a housing 11 which has an inlet 12 to allow the sample gas to enter the device, an ion generator such as an $Ni^{63}$ β emitter 14 to generate ions from the sample gas, a field gradient to accelerate the ions generated toward a collector 16 and an outlet 18 to allow the sample gas to exit the device. The collector 16 is adapted to measure total ions. A change in total ions measured indicates a change in a total concentration of impurities in the sample. The housing is preferably about six centimeters long with a diameter of five centimeters or more.

Preferably, the $Ni^{63}$ β emitter 14 is a radioactive foil of $Ni^{63}$ that emits approximately 67 keV electrons and has a strength of 1 milli Curie. However, any suitable emitter will operate satisfactorily. For example, Americium 241 can be used. Americium 241 is an alpha emitter and will work instead of the $Ni^{63}$ which is a beta emitter. The advantage of Americium 241 is that it is exempt from regulation by the Nuclear Regulatory Committee (NRC). Americium 241 has, for example, been used in smoke detectors. Tritium, a radioactive isotope of hydrogen may also be used. Tritium is a beta emitter and has been used in commercially available helium ionization detectors. Using tritium will result in the device being exempt from a six month wipe test that is required by the NRC for radioactive devices. Additionally, it is preferable that the collector 16 is connected to an amplifier 20 which is used to detect a current striking the collector. Preferably, the device is fabricated from a metal, such as electro-polished stainless steel that can be heated to at least 200 degrees Celsius.

A potential of a first voltage is applied to the foil of the $Ni^{63}$ emitter 14. Downstream of the foil is a wire mesh grid electrode 22 and it has a potential of a second voltage applied to it, where the second voltage is less than the first voltage. Downstream of the grid electrode 22, near the outlet 18 is the collector 16. This collector 16 is preferably connected to the amplifier 20 which is used to detect current striking the collector. Preferably, the collector is connected to a ground base preamplifier (not shown) such that the collector is at zero volts. The gradient along the length of the device is preferably about 200 to 300 volts per centimeter.

Changes in the composition of the sample gas will cause a change in the total number of positive ions formed. The positive ions that are formed will be accelerated due to the potential difference between the first voltage applied to the foil of the $Ni^{63}$ emitter 14 and the voltage at the collector 16. The collector 16 measures the positive ion charge. Changes in the measured current are proportional to the changes in the composition of the sample gas.

In the present invention, the $Ni^{63}$ β emitter 16 is the source of electrons rather than a corona discharge as a source of electrons, as disclosed in the prior art. The advantage of the $Ni^{63}$ is that the emission rate of electrons is governed by natural laws, and the emission will not change over the lifetime of the device of the present invention. Another advantage over the corona discharge is that no high voltage power supplies are needed to generate the electrons, thereby making the device simple and inexpensive. Since the emission remains constant, the response of the device will not change over time.

Additionally, in the present invention, the total positive ions generated in the neutral plasma formed by the emission from the $Ni^{63}$ is measured. The total positive ions can be measured using a Faraday plate collector and a sensitive preamplifier. This is easier to measure than attempting to measure change in voltage required to keep a discharge current constant.

The grid electrode 22 is not a requirement for the total impurity monitor for gases of the present invention to operate satisfactorily. However, if the monitor housing is long, one or more grid electrodes may be placed between the collector 16 and the $Ni^{63}$ emitter 14 to improve performance. The main purpose of the grid electrode 22 and the voltage differential is to facilitate ions in moving from the region of the $Ni^{63}$ emitter 14 to the collector 16.

Alternatively, the inside of the housing 11 can be coated with a resistive coating (not shown) along the length of the tube. With a resistive coating, the inside diameter of the housing can be made much smaller, for example, around 1 centimeter. With this resistive coating, a grid electrode is not required, even for longer cells.

Although illustrated and described herein with reference to specific embodiments, the present invention nevertheless is not intended to be limited to the details shown. Rather, various modifications may be made in the details within the scope and range of equivalents of the claims without departing from the spirit of the invention.

What is claimed is:

1. A device for measuring a total concentration of impurities in a sample gas, comprising a housing having an inlet to allow said sample gas at atmospheric pressure to continuously enter said housing, an emitter to continuously generate positive ions from said sample gas, a field gradient to continuously accelerate substantially all of said positive ions continuously toward a collector until substantially all of said positive ions reach said collector, said emitter having a higher voltage than the collector, said collector adapted to measure total positive ions in said sample gas, at least one grid electrode located in said housing between said emitter and said collector to facilitate ions in moving from said emitter to said collector, said emitter has a potential of a first voltage applied thereto and at least one of said at least one grid electrode has a potential of a second voltage applied thereto, where said second voltage is less than said first voltage, and an outlet to allow said sample gas to exit said housing, whereby a change in total positive ions received by said collector indicates a change in said total concentration of impurities in said sample gas.

2. The device for measuring a total concentration of impurities in a sample gas according to claim 1, wherein said emitter is a radioactive foil of $Ni^{63}$.

3. The device for measuring a total concentration of impurities in a sample gas according to claim 2, wherein said radioactive foil of $Ni^{63}$ emits approximately 67 keV electrons and has a strength of 1 milli Curie.

4. The device for measuring a total concentration of impurities in a sample gas according to claim 1, wherein said collector is connected to an amplifier used to amplify a current striking said collector.

5. The device for measuring a total concentration of impurities in a sample gas according to claim 4, including a ground base preamplifier connected between said collector and said amplifier.

6. The device for measuring a total concentration of impurities in a sample gas according to claim 1, wherein said field gradient is approximately 200 to 300 volts per centimeter.

7. The device for measuring a total concentration of impurities in a sample gas according to claim 1, including a resistive coating on an inside surface of said housing to facilitate ions in moving from said emitter to said collector.

8. The device for measuring a total concentration of impurities in a sample gas according to claim 1, wherein said housing is metal.

9. The device for measuring a total concentration of impurities in a sample gas according to claim 1, wherein said housing is fabricated from electro-polished stainless steel.

10. The device for measuring a total concentration of impurities in a sample gas according to claim 1, wherein said device can be heated to at least 200 degrees Celsius.

11. The device for measuring a total concentration of impurities in a sample gas according to claim 1, wherein said emitter is a radioactive foil of Americium 241.

12. The device for measuring a total concentration of impurities in a sample gas according to claim 1, wherein said emitter is a radioactive foil of tritium.

13. A device for measuring a total concentration of impurities in a sample gas, comprising a housing having an inlet to allow said sample gas at atmospheric pressure to continuously enter said housing, a $Ni^{63}$ emitter to continuously generate positive ions from said sample gas, a field gradient to continuously accelerate substantially all of said positive ions continuously toward a collector until substantially all of said positive ions reach said collector, said emitter having a higher voltage than the collector, said collector connected to an amplifier used to amplify a current striking said collector and adapted to measure total positive ions in said sample gas, and an outlet to allow said sample gas to exit said housing, said housing including at least one grid electrode located in said housing between said $Ni^{63}$ emitter and said collector to facilitate positive ions in moving from said $Ni^{63}$ emitter to said collector, said emitter has a potential of a first voltage applied thereto and at least one of said at least one grid electrodes has a potential of a second voltage applied thereto where said second voltage is less than said first voltage, whereby a change in total positive ions received by said collector indicates a change in said total concentration of impurities in said sample gas.

14. The device for measuring a total concentration of impurities in a sample gas according to claim 13, wherein said field gradient is approximately 200 to 300 volts per centimeter of housing.

15. The device for measuring a total concentration of impurities in a sample gas according to claim 13, wherein said radioactive foil of $Ni^{63}$ emits approximately 67 keV electrons and has a strength of 1 milli Curie.

16. The device for measuring a total concentration of impurities in a sample gas according to claim 13, including a ground base preamplifier connected between said collector and said amplifier.

17. The device for measuring a total concentration of impurities in a sample gas according to claim 13, wherein said housing is metal.

18. The device for measuring a total concentration of impurities in a sample gas according to claim 13, wherein said housing is fabricated from electro-polished stainless steel.

19. The device for measuring a total concentration of impurities in a sample gas according to claim 13, wherein said device can be heated to at least 200 degrees Celsius.

* * * * *